United States Patent [19]

Morrison

[11] Patent Number: 4,929,793

[45] Date of Patent: May 29, 1990

[54] PRODUCTION OF MIDDLE DISTILLATES BY PARAFFIN DISPROPORTIONATION

[75] Inventor: Roger A. Morrison, Deptford, N.J.

[73] Assignee: Mobil Oil Corporation, New York, N.Y.

[21] Appl. No.: 260,636

[22] Filed: Oct. 21, 1988

[51] Int. Cl.$^5$ .............................................. C07C 6/08
[52] U.S. Cl. ................................................... 585/708
[58] Field of Search ......................................... 585/708

[56] References Cited

U.S. PATENT DOCUMENTS 3,668,269  6/1972  Chloupek ............................. 585/708
3,953,537  4/1976  Chloupek et al. .................... 585/708

OTHER PUBLICATIONS

Engelen et al., *Applied Catalysis*, 19 (1985) 153–163.

*Primary Examiner*—Curtis R. Davis
*Attorney, Agent, or Firm*—Alexander J. McKillop; Charles J. Speciale; Malcolm D. Keen

[57] ABSTRACT

Low boiling paraffinic feedstreams such as solvent raffinates and straight run naphthas are disproportionated in the presence of an intermediate pore size zeolite such as ZSM-5 under conditions of moderately elevated temperatures and pressures to produce products boiling in the middle distillate range, such as jet fuel and diesel fuel, of highly paraffinic character.

9 Claims, No Drawings

PRODUCTION OF MIDDLE DISTILLATES BY PARAFFIN DISPROPORTIONATION

FIELD OF THE INVENTION

This invention relates to a process for producing middle distillates, especially highly paraffinic distillates such as jet fuel, by a process of disproportionating light paraffins.

BACKGROUND OF THE INVENTION

A group of products produced in large quantities by petroleum refineries is the middle distillate products, including materials such as diesel fuel, jet fuel and home heating oil. Some of these products may be relatively higher grade fuel products than others and may command a premium price as fuels products. For example, certain jet fuels of high quality may be sold as premium products with a correspondingly higher price. With a progressively increasing demand for these fuel products, there is a need for increasing the size of the fuel products pool and to this end, various synthetic and semi-synthetic processes for producing both gasoline and middle distillate products have been devised.

One process which has commended itself is the so-called MOGDL process in which light olefins, especially olefinic streams from a catalytic cracking unit, are oligomerized to products in the gasoline boiling range and above by the use of an intermediate pore size zeolite oligomerization catalyst. Processes of this type are disclosed, for example, in U.S. Patents Nos. 3,760,024, 4,211,640, 4,277,992, 4,513,156 and 4,476,330. Reference is made to these patents for descriptions of such processes. The products from these processes tend, however, to be aromatic in character under the conditions generally employed. For this reason, the middle distillate products are generally unsatisfactory for use as jet or diesel fuels which require the aromatic content to be kept at a low level.

Another semi-synthetic process which has been proposed converts low quality paraffin streams to higher value products, generally of an aromatic character, especially high octane gasoline. These processes are generally to be characterized as aromatization processes which convert the paraffins present in the feed to aromatic products, usually in the gasoline boiling range. The aromatic character of the products renders them generally unsatisfactory for use as jet or diesel fuels, although they are good blending components for the gasoline pool. Examples of such processes are to be found in U.S. Pat. No. 3,729,409 which discloses a process for upgrading a reformate feedstock containing paraffins by contacting the feed with a zeolite ZSM-5 catalyst, optionally containing a metal component, at relatively high conversion temperatures, typically from 500° to 1000° F. Similarly, U.S. Pat. No. 3,951,781 discloses a process for upgrading a straight run naphtha in combination with a solvent extracted resin and paraffinic material using a ZSM-5 catalyst, optionally with a metal component. Other aromatization processes are disclosed in U.S. Patents Nos. 4,590,323, 4,304,657 and the article by Garwood and Chen, ACS 125(1), 84(1980): "Octane Boosting Potential of Catalystic Processing of Reformate Over Shape Selective Zeolites" discloses the conversion of n-octane to benzene over a ZSM-5 catalyst with the production of only trace amounts of $C_2-$ in the product.

Given the emphasis in these proposals on the production of aromatic gasolines, it is surprising to find that paraffinic products of higher boiling point may be produced by appropriate selection of reaction conditions.

SUMMARY OF THE INVENTION

It has now been found that paraffinic middle distillate products may be produced by the disproportionation of low boiling, low molecular weight paraffin streams using intermediate pore size zeolite catalysts at relatively low to moderate temperatures, typically below 500° F. (about 260° C.).

According to the present invention there is therefore provided a process for making a middle distillate fuel product, typically having a boiling range in the range of 330° to 645° F. (about 165° to 345° C.) by disproportionating a light paraffinic stream in the presence of an acidic, solid, porous catalyst comprising an intermediate pore size zeolite, optionally with a metal hydrogenation component such as platinum. The reaction is carried out at moderately elevated temperatures up to about 500° F. (about 260° C.) and preferably under elevated pressures, usually at least 50 psig (about 446 kPa abs.) and preferably from 400 to 1000 psig (about 2460 to 70900 kPa abs.). It has been found that the use of these conditions results in a product which is predominantly paraffinic in character and which is useful as a premium quality jet fuel or as other paraffinic distillates including diesel fuel. Thus, the present process provides a way of converting low quality paraffin streams such as solvent raffinates or $C_5-C_6$ straight run naphthas to premium quality distillate fuels.

DETAILED DESCRIPTION

The feed used in the present process is a light i.e. low boiling stream which is essentially paraffinic in character i.e. contains no significant amounts of aromatics. Streams of this kind may typically comprise $C_5-C_6$ straight run naphthas, low boiling solvent raffinates obtained from petrochemical processing such as raffinates obtained from the solvent extraction processes such as UDEX extraction or sulfolane extraction and other similar petroleum refinery streams. The UDEX and sulfolane processes are disclosed in *Modern Petroleum Technology*, Hobson, G.D. (Ed.), Applied Science Publishers Ltd., Barking, 1973, pp. 409-410 to which reference is made for a description of these processes. Streams of this kind can be characterized as $C_5-C_8$ streams although minor amounts of $C+_9$ paraffins may be present, typically in amounts not more than about 1% by weight. Generally, the streams will have at least 60% by weight in the $C_5$ to $C_7$ boiling range and will usually contain less than 5wt% aromatics, typically benzene and toluene. A particular advantage of the present process, however, is that the aromatic content of the feed is significantly reduced during processing so that the final product is almost entirely paraffinic in character, rendering it highly suitable for use as a jet fuel or diesel fuel.

The feed is contacted with an intermediate pore size zeolite under conditions of moderately elevated temperature and pressure. The zeolitic catalyst may contain a metal hydrogenation component such as platinum or palladium although this is not essential to the process. If present, such metal components will typically be present in amounts up to about 1 wt.% based on the catalyst, usually from 0.1 to 0.5 wt.% based on the catalyst. The catalyst may also include a binder such as alumina, silica or silica-alumina for added mechanical strength.

The essential component of the catalyst is an intermediate pore size zeolite such as ZSM-5, ZSM-11, ZSM-22, ZSM-23 or another zeolite having a Constraint Index from 1 to 12. The specified zeolites are known materials. Constraint Index may be determined by the method disclosed in U.S. Pat. No. 4,016,218 to which reference is made for a description of the method of determining the index. The significance of Constraint Index as an indicium of zeolite structure is disclosed in J. Catalysis 67, 218–222 (1981) to which reference is also made.

The process is carried out, as mentioned above, under conditions of moderately elevated temperature and pressure with temperatures from 400° to 500° F. (about 205° to 260° C.) being preferred. Pressures of at least 50 psig should be employed and pressured of about 400 to 1000 psig (about 2460 to 7000 kPa abs) are preferred. Space velocity is maintained at moderate values, typically from 0.5 to 2 WHSV and in addition, no hydrogen is added to the feed. Under these conditions, a significant degree of paraffin disproportionation takes place and typically, $C_7$ paraffins disproportionate to $C_4$ to $C_6$ lower molecular weight paraffins with $C_8$ to $C_{10}$ paraffins being produced simultaneously. This type of reaction is distinct from the aromatization type reactions encountered in the known processes referred to above operating at relatively high temperatures and low pressures. Disproportionation to a higher molecular weight product in the middle distillate boiling range occurs and a notable feature of the process is that the product obtained by the disproportionation may contain a lower amount of aromatics than the feed. Product recovery may take place by suitable fractionation of the effluent stream from the disproportionation process.

EXAMPLES 1 TO 4

A $C_5$ to $C_9$ UDEX raffinate was used as the feedstock for a disproportionation process employing a Pt/ZSM-5 catalyst (0.18 wt. % Pt, 65% zeolite, zeolite $SiO_2$: $Al_2O_3 = 67$). The UDEX raffinate was passed over the catalyst in the absence of added hydrogen at temperatures from about 400 to 500° F. at pressures from 50 to 800 psig at 1 WHSV. The product distributions under different conditions are shown in Table 1 below.

TABLE 1

Conversion of Beaumont UDEX Raffinate Over Pt/ZSM-5

| | | | | | UDEX RAFFINATE |
|---|---|---|---|---|---|
| TEMPERATURE,°F. | 426.00 | 476.00 | 451.00 | 501.00 | |
| PRESSURE,PSIG | 800.00 | 800.00 | 50.00 | 50.00 | |
| WHSV | 1.00 | 1.00 | 1.00 | 1.00 | |
| H2.HC | 0.00 | 0.00 | 0.00 | 0.00 | |
| MATERIAL BALANCE | 95.89 | 95.51 | 97.84 | 105.15 | |
| TIME ON STREAM, HRS. | 20.20 | 24.30 | 43.30 | 47.80 | |
| PRODUCT DIST., WT % | | | | | |
| C1 | 0.00 | 0.00 | 0.00 | 0.00 | |
| C2 | 0.00 | 0.09 | 0.00 | 0.04 | |
| C2= | 0.00 | 0.00 | 0.00 | 0.00 | |
| C3 | 0.91 | 3.97 | 0.46 | 3.17 | |
| C3= | 0.00 | 0.00 | 0.01 | 0.04 | |
| ISO-C4 | 1.62 | 4.51 | 0.50 | 2.53 | |
| N-C4 | 1.41 | 4.26 | 0.54 | 3.13 | |
| C4= | 0.00 | 0.00 | 0.06 | 0.18 | |
| ISO-C5 | 2.57 | 4.31 | 1.73 | 2.96 | 0.96 |
| N-C5 | 5.88 | 6.11 | 5.86 | 6.89 | 3.96 |
| C5= | 0.00 | 0.01 | 0.09 | 0.11 | 0.01 |
| 2,2 DM-C4 | 0.37 | 0.37 | 0.36 | 0.36 | 0.33 |
| CYCLO-C5 | 2.58 | 1.98 | 2.71 | 2.45 | 2.13 |
| 2,3 DM-C4 | 0.85 | 0.83 | 0.82 | 0.82 | 1.42 |
| 2-M-C5 | 7.05 | 6.79 | 6.80 | 6.88 | 6.30 |
| 3-M-C5 | 5.65 | 5.67 | 5.60 | 5.61 | 5.40 |
| N-C6 | 9.09 | 5.85 | 11.05 | 8.60 | 10.41 |
| C6= | 0.00 | 0.00 | 0.00 | 0.00 | 0.14 |
| M-CYCLO-C5 | 5.03 | 3.92 | 5.42 | 4.82 | 5.60 |
| BENZENE | 0.00 | 0.00 | 0.17 | 0.16 | 0.21 |
| CYCLO-C6 | 1.43 | 1.23 | 1.32 | 1.20 | 1.85 |
| C7'S | 34.08 | 29.98 | 35.22 | 31.84 | 37.16 |
| N-C7 | 8.19 | 4.11 | 9.76 | 5.47 | 11.85 |
| TOLUENE | 1.04 | 0.82 | 1.81 | 1.66 | 2.91 |
| C8'S | 5.92 | 5.36 | 6.02 | 5.01 | 7.08 |
| N-C8 | 0.81 | 0.60 | 0.85 | 0.44 | 1.14 |
| C8 AR. | 0.66 | 1.00 | 0.79 | 1.29 | 0.86 |
| C9+PAR. | 0.20 | 0.27 | 0.09 | 0.10 | 0.28 |
| C9 AR.+ PAR MADE | 4.66 | 7.95 | 1.95 | 4.24 | 100.00 |
| C10 AR. | 0.00 | 0.00 | 0.00 | 0.00 | |
| C10–C12 AR. | 0.00 | 0.00 | 0.00 | 0.00 | |
| NAPHTHALENES | 0.00 | 0.00 | 0.00 | 0.00 | |
| M-NAPHTHALENES | 0.00 | 0.00 | 0.00 | 0.00 | |
| C13 + 'S | 0.00 | 0.00 | 0.00 | 0.00 | |
| WT % NON-C6 CONV | 13.68 | 27.36 | 8.28 | 19.99 | |
| TO C1-C4 | 3.94 | 12.83 | 1.57 | 9.09 | |
| SELECTIVITY, WT % | | | | | |
| C1-C4 | 28.80 | 46.89 | 18.96 | 45.47 | |
| C5'S | 25.80 | 20.10 | 33.22 | 25.16 | |
| C9+'S | 34.06 | 29.06 | 23.55 | 21.21 | |
| TOTAL SEL TO C1-C4, | 88.66 | 96.05 | 75.73 | 91.84 | |

We claim:

1. A process for producing distillate range products by disproportionating a $C_5$ to $C_8$ paraffinic feedstream boiling below the distillate boiling range in the presence of an acidic, solid, porous catalyst comprising an intermediate pore size zeolite at a pressure from 50 to 100 psig and recovering a paraffinic distillate range product.

2. A process according to claim 1 in which the feedstream comprises a solvent raffinate.

3. A process according to claim 1 in which the zeolite comprises ZSM-5.

4. A process according to claim 1 in which the catalyst includes a platinum or palladium hydrogenation component.

5. A process according to claim 1 which is carried out at a temperature from 400° to 500° F.

6. A process according to claim 1 in which the feed contains no more than 5 wt.% benzene and toluene.

7. A process according to claim 1 in which the paraffinic product is essentially free of $C^+_{10}$ aromatics.

8. A process according to claim 1 in which the aromatic content of the paraffinic product is lower than that of the feed.

9. A process according to claim 1 which is carried out at a pressure of from 400 to 1000 psig.

* * * * *